United States Patent [19]
Posey et al.

[11] Patent Number: 6,126,647
[45] Date of Patent: Oct. 3, 2000

[54] MAGNETICALLY GUIDED CATHETER WITH SENSOR

[75] Inventors: David Tyler Posey, Chickasha; Raymond Lee Morgan, Norman, both of Okla.

[73] Assignee: Hermetic Switch, Inc., Chickasha, Okla.

[21] Appl. No.: 09/313,456

[22] Filed: May 17, 1999

[51] Int. Cl.[7] ............................................. A61M 31/00
[52] U.S. Cl. ............................................ 604/270; 600/12
[58] Field of Search .................................. 604/270, 523, 604/529, 500, 508; 600/9, 12, 13

[56] References Cited

U.S. PATENT DOCUMENTS

| | | | |
|---|---|---|---|
| 4,077,412 | 3/1978 | Moossun | 604/270 X |
| 4,364,377 | 12/1982 | Smith | 600/12 |
| 5,176,618 | 1/1993 | Freedman | 600/12 |
| 5,431,640 | 7/1995 | Gabriel | 604/270 |

*Primary Examiner*—John D. Yasko
*Attorney, Agent, or Firm*—James T. Robinson

[57] ABSTRACT

A traction position indicator for a feeding tube catheter provides a permanent magnet and a sensor, both in the distal end portion of the catheter, wherein the sensor is responsive to the presence of a magnetic field of predetermined strength supplied by an external magnet. The external magnet forms a magnetic coupling with the catheter magnet to permit manipulation of the catheter in response to movement of the external magnet. The sensor responds to the magnetic field of the external magnet, but only when the external magnet and the catheter magnet are magnetically coupled sufficiently to create a traction force so that the catheter distal end portion can be manipulated by movement of the external magnet.

Apparatus for creating a magnetic guidance path for a remote device includes a follower magnet and a sensor, both of which are attached to the remote device, and a leader magnet. The leader magnet forms a magnetic guidance path by permeating the location of the remote device to form a magnetic coupling between the leader magnet and the follower magnet. The sensor responds to the magnetic field provided by the leader magnet when—and only when—the leader magnet and the follower magnet are magnetically coupled sufficiently to permit manipulation of the follower magnet by movement of the leader magnet.

70 Claims, 6 Drawing Sheets

6,126,647

MAGNETICALLY GUIDED CATHETER WITH SENSOR

BACKGROUND OF THE INVENTION

1. Field of the Invention

The present invention relates to a medical catheter, and more particularly, but not by way of limitation, to an improved catheter feeding tube having a permanent magnet on the distal end portion so that the distal end portion can be steered within a patient's body by an external magnet. The improvement according to the present invention provides a sensor which, as the external magnet is moved toward the patient's abdomen, indicates the point at which the permanent magnet in the distal end portion of the catheter is captured by the magnetic field of the external magnet. As used herein, the terms captured or capture are used to indicate a condition in which the distal end portion of the catheter will move within the patient's body in response to movement of the external magnet adjacent the patient's abdomen. The term traction position will be used to indicate the farthest position of the external magnet from the catheter distal end portion which results in capture of the distal end portion by the magnetic field of the external magnet.

2. Discussion

U.S. Pat. No. 5,431,640, Gabriel, discloses a method and apparatus for intubation of a patient. A force couple is established between a permanent magnet in the catheter tip and a external permanent magnet. The force couple imparts a traction force to the catheter tip for advancing movement of the catheter tip in the direction of bolus in the stomach beyond the pyloric sphincter and into the duodenum.

The use of magnetic field produced by an external magnet to maneuver a catheter to the distal duodenum of a patient requires precise knowledge of the anatomy of the stomach and duodenum in relation to the abdominal surface of the patient. This knowledge is necessary so the operator can maneuver the external magnet over the abdomen of the patient in a precise path resulting in advancement of the catheter through the stomach and into the duodenum of the patient. An operator maneuvering an external magnet can not see through the abdominal wall to decide whether the distal end portion of the catheter is continuously captured by the magnetic field of the external magnet during the advancement of the catheter. Thus, an additional procedure is required to determine whether the distal end of the catheter is properly advancing into the patient's duodenum.

One method involves the use of X-ray monitoring to confirm the position of the distal end of the catheter. Another method, described in U.S. Pat. No. 5,431,640, requires the aspiration of fluid from the distal end of the catheter and the measurement of the pH of the aspirated fluid. However, pH values for a particular patient may vary from expected values, thereby resulting in false position information. What is needed is an apparatus for advancing the distal end portion of a catheter using the field of an external magnet which provides an indication whether the distal end of the catheter is being properly advanced into the patient's duodenum.

SUMMARY OF THE INVENTION

The present invention provides a feeding tube catheter having a distal end portion containing a permanent magnet and sensor responsive to the presence of a magnetic field or flux of a predetermined strength. The present invention further includes an external magnet for manipulating the distal end portion of the feeding tube catheter. The sensor in the distal end portion is selected to respond to a magnetic field, such as that provided by the external magnet, but only when the external magnet and the catheter magnet are magnetically coupled sufficiently to create a traction force so that the catheter distal end portion can be manipulated by movement of the external magnet. That is, the sensor provides an indication when the external magnet is in the traction position with respect to the catheter magnet.

The present invention further provides apparatus for creating a magnetic guidance path for a remote device containing a follower magnet and sensor. A leader magnet forms a magnetic guidance path by permeating the location of the remote device, the field of magnetic flux being sufficiently dense to impart a traction force to the follower magnet through a flux coupling between the magnetic flux of the follower magnet and the magnetic flux of the leader magnet. The present sensor is selected to respond to the magnetic field provided by the leader magnet, but only when the leader magnet and the follower magnet are magnetically coupled sufficiently to permit manipulation of the follower magnet by movement of the leader magnet. The sensor provides an indication when the leader magnet is an the traction position with respect to the follower magnet.

An object of the present invention is to provide a catheter which is more easily and accurately positioned than the catheters currently available.

Another object of the present invention is to apparatus for guiding a remote device magnetically, using a sensor to indicate when manipulation of the remote device is possible.

Other objects, features, and advantages of the present invention will become clear from the following description of the preferred embodiment when read in conjunction with the accompanying drawings and claims.

DETAILED DESCRIPTION OF THE INVENTION

In the following description of the invention, like numerals and characters designate like elements throughout the figures of the drawings.

Figure 1:
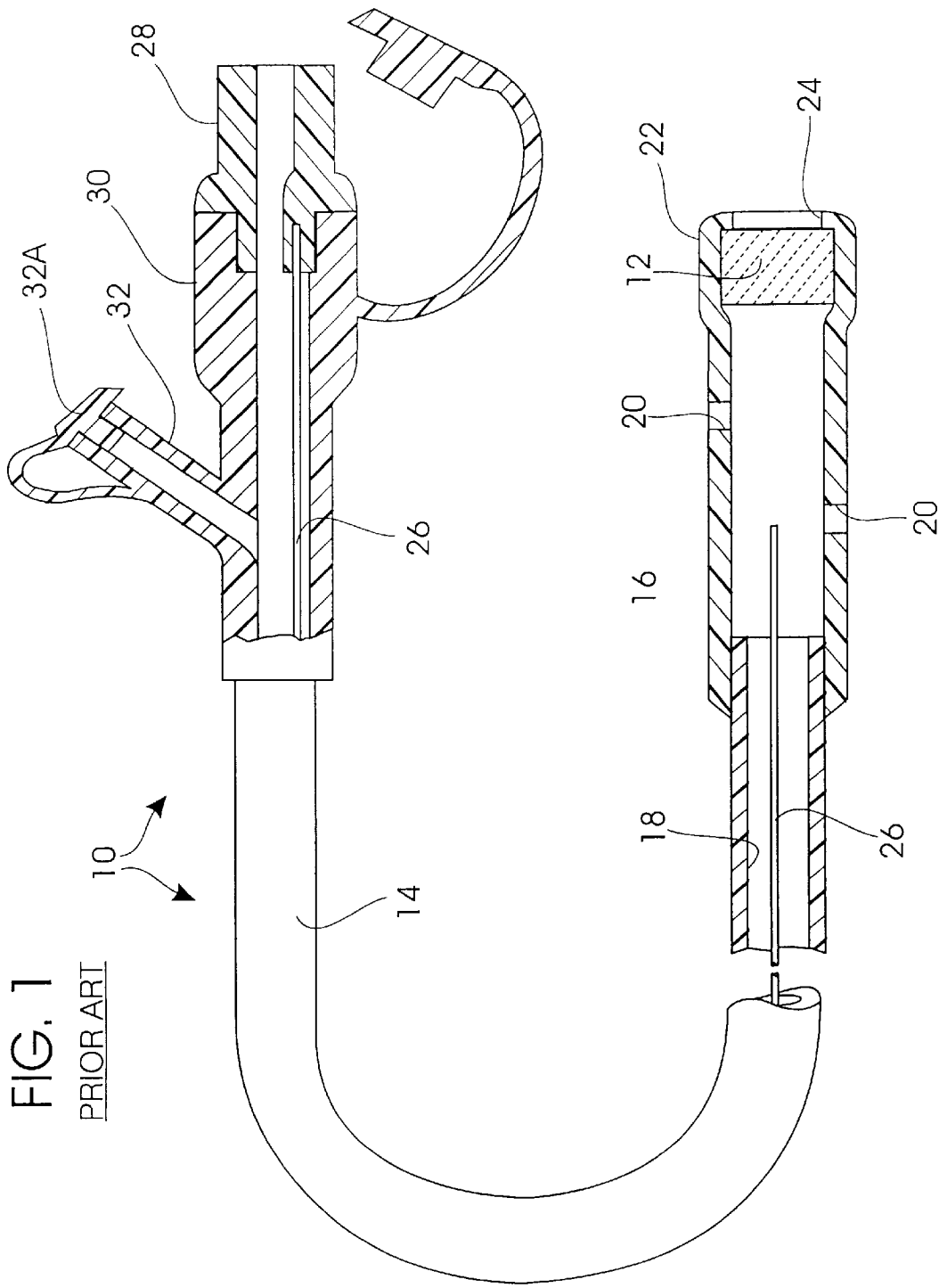
FIG. 1 (prior art) is a partial cross-sectional view of the medical intubation apparatus disclosed in U.S. Pat. No. 5,431,640, Gabriel.

FIG. 1 (prior art) illustrates the feeding tube catheter disclosed in U.S. Pat. No. 5,431,640, Gabriel. A feeding tube catheter 10 includes a permanent magnet 12 and a radio opaque body portion 14. At the distal end of the catheter 10 a radio opaque tip portion 16 adheres to the end part of the body portion 14. A lumen 18 in the body portion 14 forms a fluid conducting relation with the internal cavity of the tip portion 16 which contains eyelet apertures 20 spaced along the length of the tip portion 16 for discharging and receiving fluids to the small intestine of the patient. The magnet 12, which has a diameter slightly larger than the inside diameter of the radio opaque portion 16, produces a slight bulge 22 when placed in the distal end of the tip portion 16. The magnet can be inserted through an opening 24 in the end wall of the tip portion 16.

Still referring to FIG. 1 (prior art), the feeding tube catheter 10 of U.S. Pat. No. 5,431,640 includes a stylet 26 anchored in a cap 28 and extending along the entire length of the lumen 18. The stylet 26 adds a desired degree of stiffness and rigidity to the catheter 10 to facilitate placement. The cap 28 is used for extracting the stylet 26 after the catheter 10 has been placed in the patient. The cap 28 is fitted to a cavity formed in a fixture 30 joined to the free end of the catheter 10 opposite the tip portion 16. An additional duct section 32 having a removable closure cap 32A provides access when it is desired to introduce or withdraw fluids from the lumen 18 of the feeding tube catheter 10.

The feeding tube catheter 10 of the U.S. Pat. No. 5,431,640 patent is designed for manipulation by an external permanent magnet having at least 300 Gauss at a distance of 4 inches from the magnet's pole face. The external permanent magnet forms a magnetic coupling with the magnet 12 in the feeding tube catheter 10 so that the attractive force between the external permanent magnet and the magnet 12 (i.e., the traction force) permits medical personnel to advance the tip portion 16 of the catheter through the patient's stomach and into the patient's duodenum by manipulation of the external magnet. The position of the external permanent magnet with respect to the catheter magnet 12 at which the traction force is sufficient to advance the catheter tip portion 16 is referred to as the traction position.

Figure 2:
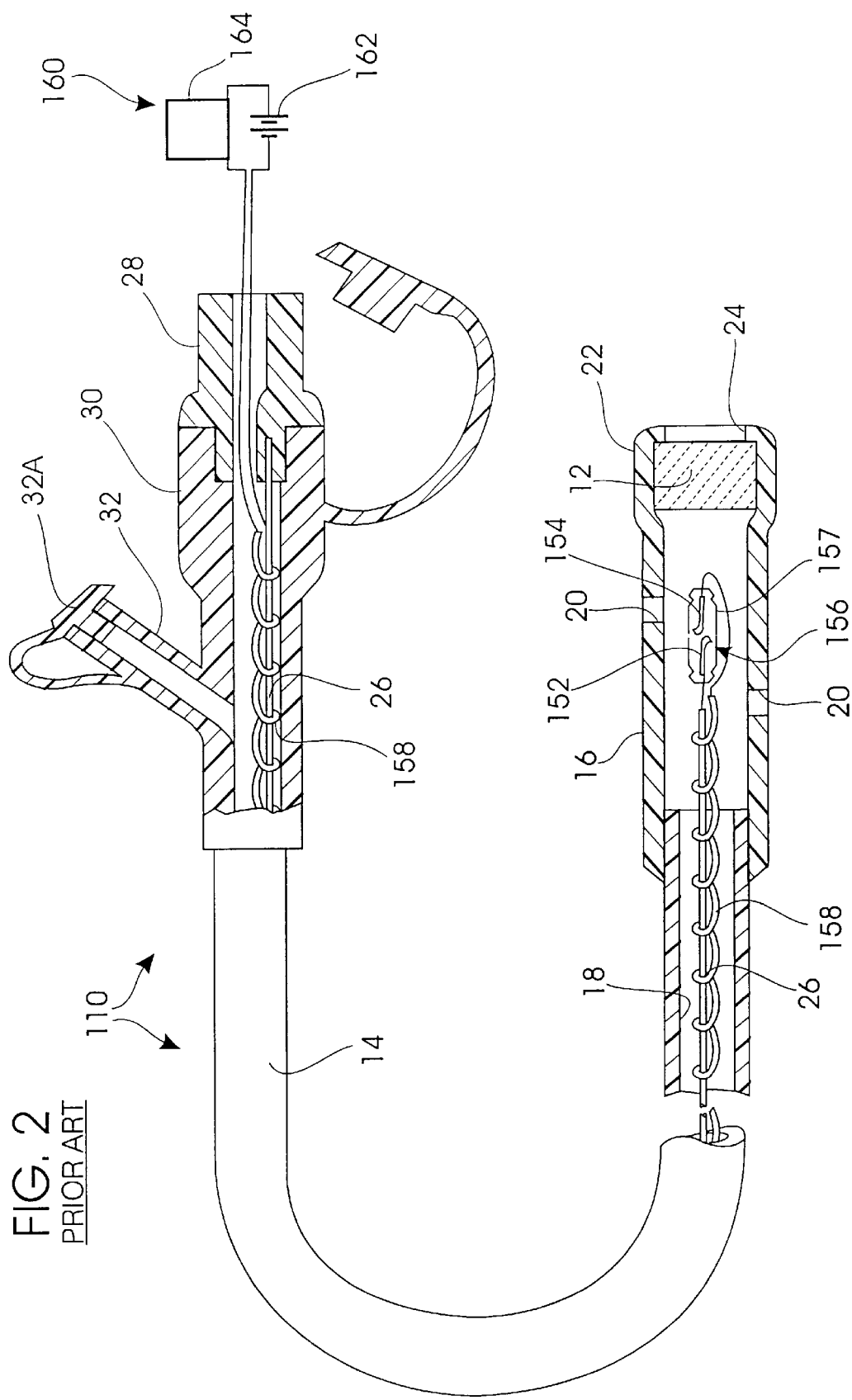
FIG. 2 (prior art) is a partial cross-sectional view of a proposed improved medical intubation apparatus utilizing a sensor.
Figure 3:
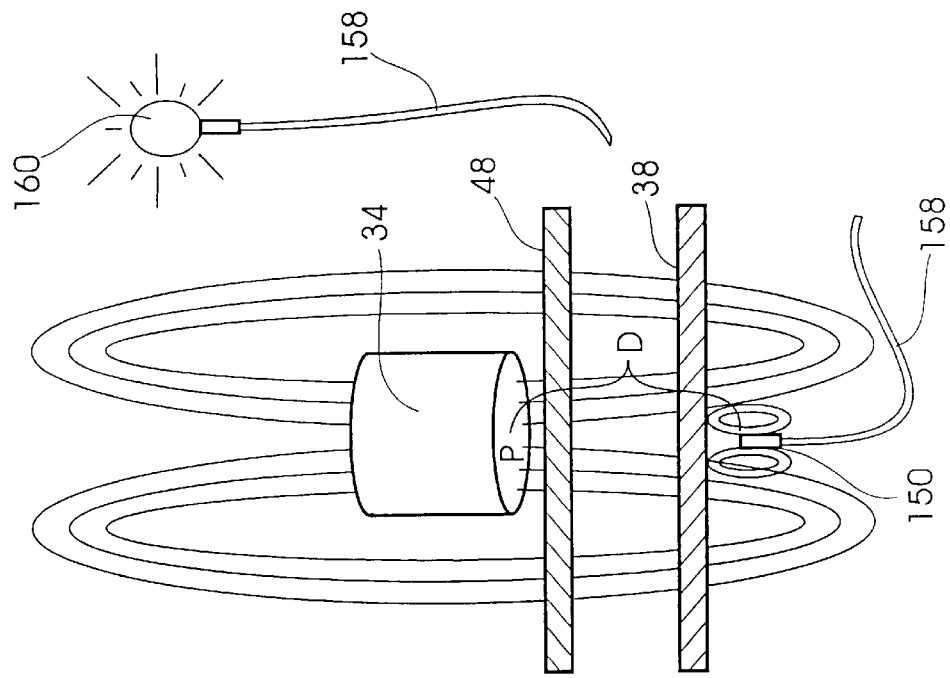
FIG. 3 (prior art) is a representation of the operation of the device of FIG. 2.
Figure 4:
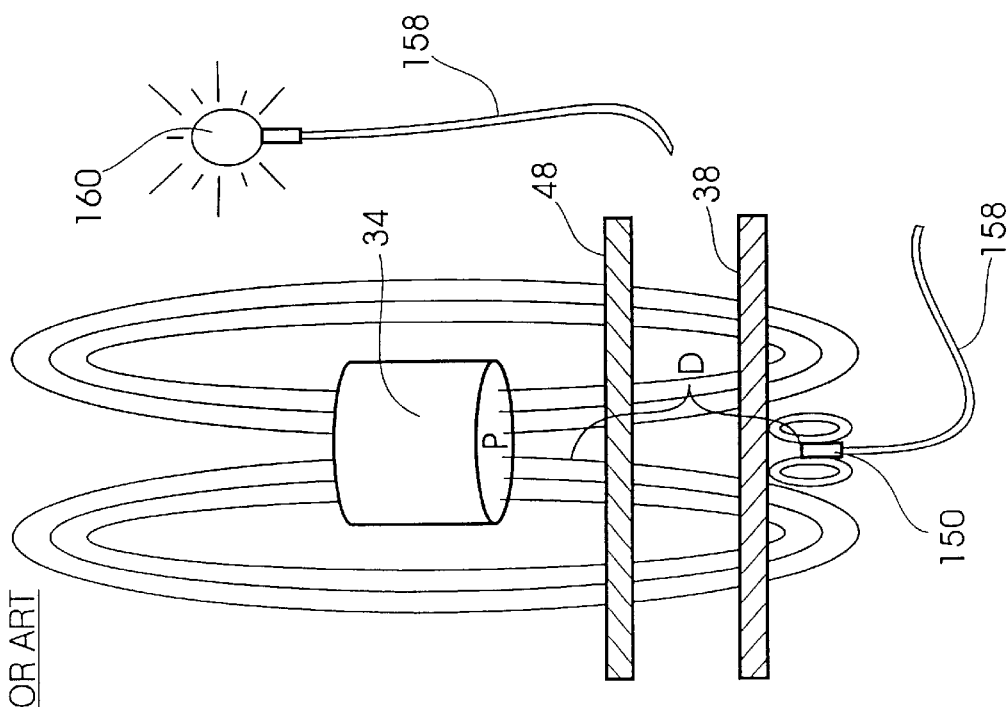
FIG. 4 (prior art) is another representation of the operation of the device shown in FIG. 2.

Referring now to FIGS. 2–4 (prior art), the feeding tube catheter 10 illustrated in FIG. 1 has been modified to produce a feeding tube catheter 110. A sensor 156 is positioned in the tip portion 16 of the catheter 110. The sensor 156 is a magnetic reed switch which includes reeds 152, 154 sealed in a glass envelope 157. Leads 158 connect the sensor 156 to a signal generator 160. The signal generator includes a battery 162 which supplies power to a signal device 164 when the reeds 152, 154 close in response to a magnetic field supplied by an external permanent magnet (FIGS. 3–4).

Still referring to FIGS. 2–4 (prior art), the purpose of the sensor 156 is to provide a signal when—and only when—the magnet 12 in the distal end of the tip portion 16 is magnetically coupled with an external magnet 34 (FIGS. 3 and 4) sufficiently to create a traction force. Stated another way, the sensor 156 should provide a signal when the external magnet 34 is in the traction position. The signal generator 160 should not provide a signal when the external permanent magnet 34 is not capable of manipulating the tip portion 16 of the feeding tube catheter 110.

The operation of the modified feeding tube catheter 110 is illustrated in FIGS. 3 and 4. A distance D in FIGS. 3 and 4 defines a traction position by indicating the distance at which the external permanent magnet 34 becomes magnetically coupled with the magnet 12 in the distal end portion 150 of the tip portion 16 so that movement of the external permanent magnet 34 produces a corresponding movement of the distal end portion 150 of the feeding tube catheter 110. The distance D, which generally represents the distance between the interior of the patient's stomach wall 38 and the exterior of the patient's abdominal wall 48, is about 3.5 inches to 5.0 inches.

Referring now to FIG. 3 (prior art), the external permanent magnet 34 (also referred to herein as the leader magnet) is positioned out of range of the minimum distance required to form a magnetic coupling with the distal end portion 150 sufficient to permit manipulation of the distal end portion 150 by the external permanent magnet 34. The distal end portion includes the permanent magnet 12 (FIG. 2), which is sometimes referred to herein as a follower magnet. As shown in FIG. 3, the signal generator 10 (illustrated as energizing a light bulb) has been actuated although the external permanent magnet 34 is beyond the minimum distance D required for formation of a magnetic coupling of sufficient strength to permit manipulation of the distal end portion 150 (containing the follower magnet 12) in response to movement of the external permanent magnet 34.

As used herein, the term traction position is defined to mean the position of the external permanent magnet 34 (i.e, the leader magnet) from the distal end portion 150 of the feeding tube catheter 110 containing a magnet 12 (i.e., the follower magnet) at which the magnetic coupling between the leader magnet 34 and the follower magnet 12 is sufficient to permit manipulation of the distal end portion 150 by movement of the leader magnet 34. As indicated in FIGS. 3 and 4, the distance D defines the traction position.

Referring now to FIG. 4 (prior art), the external permanent magnet 34 is shown in the traction position, and the sensor 156 (FIG. 2) has actuated the signal generator 160, as shown by the energized light bulb. Thus the modified feeding tube catheter 110 does not work as intended. The signal generator 160 is actuated prematurely (FIG. 3) due to the very strong magnetic field associated with the external magnet 34 (the leader magnet).

Figure 5:
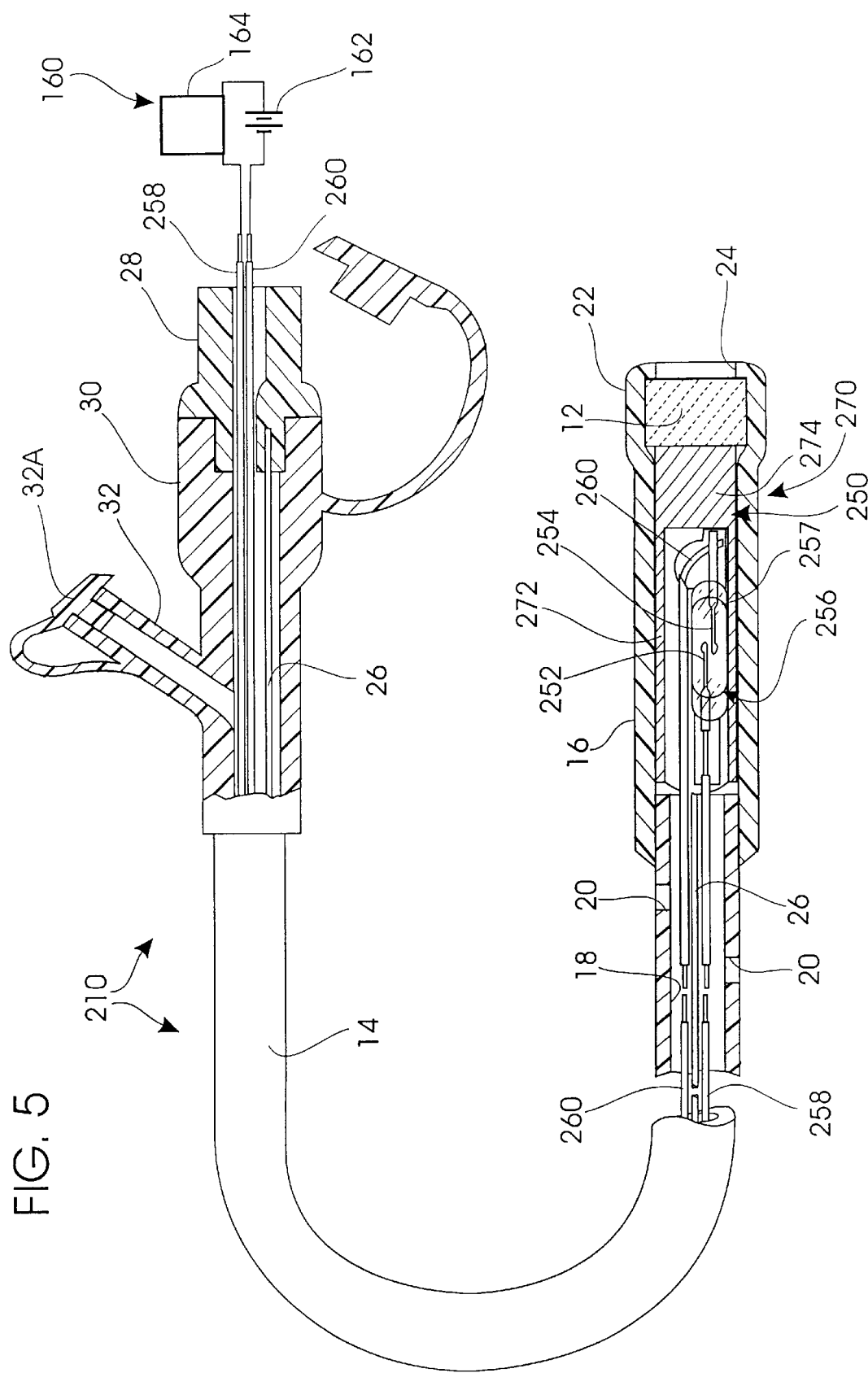
FIG. 5 is a partial cross-sectional view of applicants improved medical intubation apparatus utilizing a magnetically shielded sensor.

Referring now to FIG. 5, applicants feeding tube catheter 210 includes a sensor 256 positioned in the tip portion 16. The sensor 256 is a high ampere-turn magnetic reed switch which includes relatively stiff reeds 252, 254 sealed in a glass envelope 257. Leads 258, 260 connect the sensor 256 to a signal generator 160. The magnetic reed switch (252, 254, 257) is disposed within a ferrous metal housing 270 having the general shape of a tube closed at one end. The ferrous metal housing includes tubular walls 272 closed at one end to form a thickened end 274. The tubular ferrous metal housing 270 acts a magnetic shield to prevent premature closure of the reeds 252, 254 by the magnetic field associated with the external permanent magnet 34 (see FIGS. 9 and 10). Specifically, the ferrous metal housing 270 must become saturated before the magnetic field associated with the external permanent magnet 34 affects the reeds 252, 254. Viewed another way, as the external permanent magnet 34 is moved progressively closer to the sensor 256, the ferrous metal housing 270 deflects or redirects the lines of magnetic flux away from the reeds 252, 254 until the applied magnet field (in this case, the magnetic field associated with the external permanent magnet 34) is sufficiently strong to penetrate the magnetic shield associated with the ferrous metal housing 270 and effect closure of the reeds 252, 254.

Figure 6:
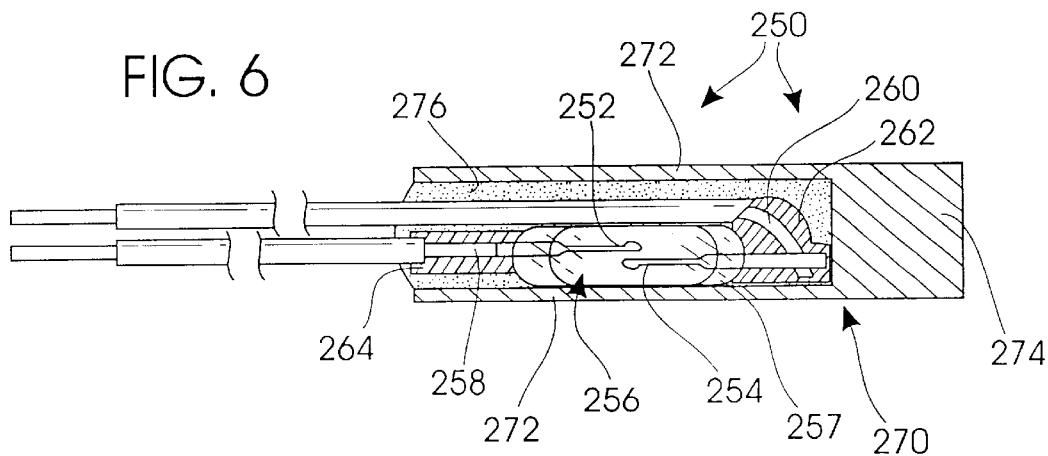
FIG. 6 is an enlarged cross-sectional view of the magnetically shielded sensor of the present invention.
Figure 7:
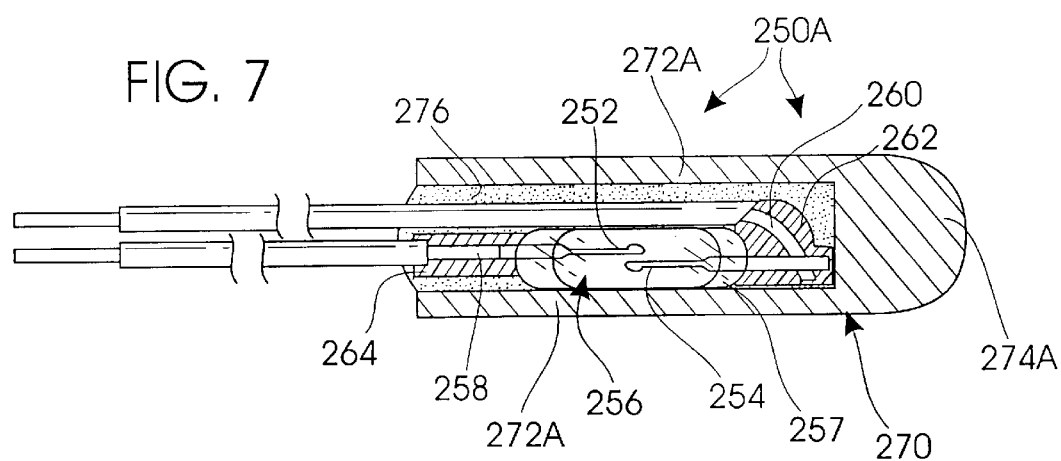
FIG. 7 is an enlarged cross-sectional view of a second embodiment of the magnetically shielded sensor of the present invention.
Figure 8:
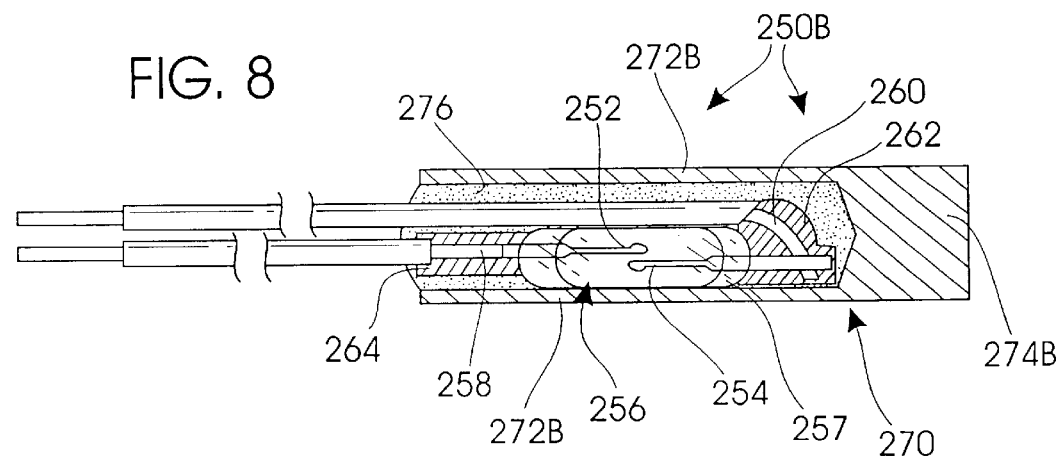
FIG. 8 is an enlarged cross-sectional view of a third embodiment of the magnetically shielded sensor of the present invention.

Referring now to FIGS. 6–8, shown therein are three embodiments of the sensor 256 and the ferrous metal housing 270 of the present invention. In FIG. 6, the magnetic reed switch, consisting of reeds 252, 254 sealed in a glass envelope 257, is disposed within the ferrous metal housing 270. The leads 258, 260 are soldered to the external portions of the reeds 252, 254, and heatshrink 262, 264 is applied as indicated. The reed switch assembly is then placed within the ferrous metal housing 270 and potting compound 276 is used to hold the reed switch and leads in position. For an external permanent magnet 34 having a magnetic flux field of about 350 Gauss at a distance of 4 inches from the pole face P (FIGS. 3, 4, 9, and 10), a ferrous metal housing 270 having a diameter of about 0.125 inch, a tubular wall 272 thickness of about 0.0125 inches, and a thickened end 274 of about 0.125 inches at its maximum thickness resulted in actuation of the signal generator 160 only when the external permanent magnet 34 was within 3.5 to 5.0 inches of the magnetic reed switch, the range established by Gabriel for creation of the traction force necessary to permit manipulation of the feeding tube catheter (either 10, 110, or 210) by the external permanent magnet 34. In the absence of the ferrous metal housing 270, the reeds 252, 254 closed at a distance of about 12–18 inches between the external permanent magnet and the magnetic reed switch.

Referring now to FIG. 7, shown therein is another embodiment of the sensor 256 and the ferrous metal housing 270 of the present invention. In FIG. 7, the tubular wall 272A is about 0.025 inches thick and the ferrous metal housing is about 0.151 inches in diameter. The thickened end portion 274A is about 0.125 inches thick at its maximum.

FIG. 8 shows another embodiment of the sensor 256 and the ferrous metal housing 270 of the present invention. In FIG. 8, the thickness of the tubular wall 272B is about 0.0125 inches and the thickened end 274B is about 0.125 inches thick at its thickest point.

In FIGS. 6–8, the ferrous metal housing 270 is annealed to a full soft condition to maximize magnetic permeability.

Figure 10:
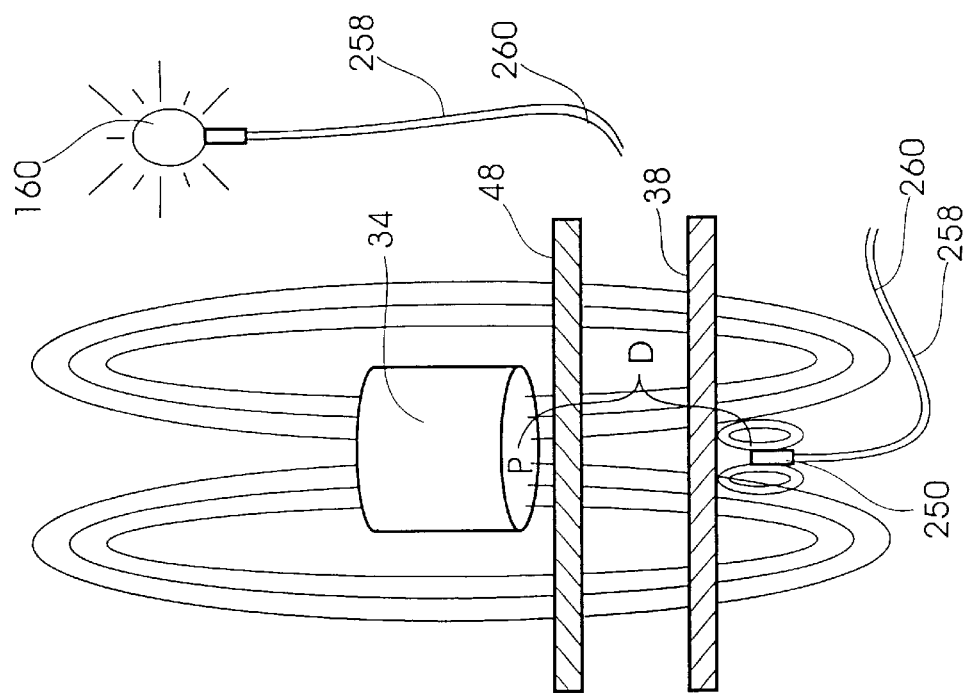
FIG. 10 is another representation of the operation of applicants invention.
Figure 9:
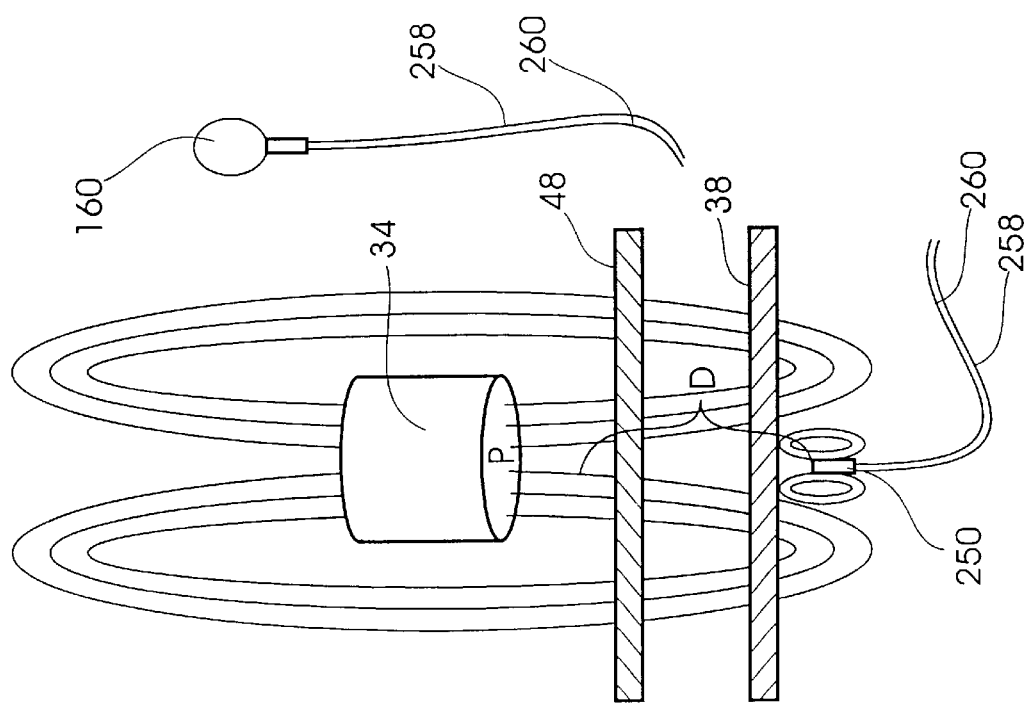
FIG. 9 is a representation of the operation of applicants invention.

The operation of the feeding tube catheter 210 is illustrated in FIGS. 9 and 10. A distance D in FIGS. 9 and 10 defines the traction position, i.e., the distance at which the external permanent magnet 34 becomes magnetically coupled with the magnet 12 in the distal end portion 250 of the tip portion 16 so that movement of the external permanent magnet 34 produces a corresponding movement of the distal end portion 250 of the feeding tube catheter 110. The distance D, which generally represents the distance between the interior of the patient's stomach wall 38 and the exterior of the patient's abdominal wall 48, is about 3.5 inches to 5.0 inches.

Referring now to FIG. 9, the external permanent magnet 34 (also referred to as the leader magnet) is positioned out of range of the minimum distance required to form a magnetic coupling with the distal end portion 250 sufficient to permit manipulation of the distal end portion 250 by the external permanent magnet 34. The distal end portion includes the permanent magnet 12 (FIGS. 1, 2, and 5), which is sometimes referred to herein as a follower magnet. As shown in FIG. 9, the signal generator 160 is not actuated so long as external permanent magnet 34 is beyond the minimum distance D required for formation of a magnetic coupling of sufficient strength to permit manipulation of the distal end portion 250 (containing the follower magnet 12) in response to movement of the external permanent magnet 34.

Referring now to FIG. 10, the external permanent magnet 34 is shown in the traction position, and the sensor 256 (FIG. 2) has actuated the signal generator 160, as shown by the energized light bulb. Thus the modified feeding tube catheter 210 performs as desired. The signal generator 160 is not actuated prematurely by the very strong magnetic field associated with the external magnet 34 (the leader magnet).

It will be understood by one skilled in the art that the ferrous metal housing 270, which acts as a magnetic shield to prevent the reeds 252, 254 from closing prematurely, can be altered to produce a sensor which actuates the signal generator at a particular specified operating distance between the housed magnetic reed switch and the external permanent magnet. A relatively thinner tubular wall 272, 272A, 272B will result in actuation of the signal generator at a greater operating distance. A relatively thinner thickened end 274, 274A, 272B will also result in actuation of the signal generator at a greater operating distance. Selection of the magnetic reed switch also affects the operating distance. A magnetic reed switch having relatively more flexible reeds results in actuation of the signal generator at a greater operating distance, whereas a magnetic reed switch have relatively stiffer reeds results effectively reduces the distance at which the signal generator is actuated.

While applicants' invention is illustrated herein as being a normally open magnetic reed switch 256 disposed within a ferrous metal housing 270, it will be understood to one skilled in the art that reed switches can be either normally open or normally closed. A single-pole, single-throw (SPST), normally-open magnetic reed switch (also referred to by those skilled in the art as a Form "A" reed switch) is illustrated herein. Single-pole, single-throw (SPST), normally-closed magnetic reed switches (also referred to by those skilled in the art as Form "B" reed switches), single-pole, double-throw (SPDT), and break-before-make reed switches (also referred to by those skilled in the art as Form "C" reed switches) are known in the art and suitable for use in lieu of the magnetic reed switch 16 of FIGS. 5–8. Whether Form A, Form B, or Form C, each type of switch can be shielded in accordance with the present invention as taught herein.

It will be further understood by one skilled in the art that the present invention, separate and apart from its application with a feeding tube catheter, is for apparatus involving a magnetic reed switch disposed within a housing for use with a leader magnet and a follower magnet, so that, for a leader magnet having a specified magnetic field strength, the reed switch closes at a specified distance. Thus, for any application in which a leader magnet is used to manipulate a follower magnet, the present invention will actuate a signal generator at a distance previously determined to create the traction force necessary for the leader magnet to manipulate the follower magnet.

It will be further understood by one skilled in the art that the leader magnet can be used to manipulate the follower magnet to assist in pulling copper wires through hollow walls, in manipulating fiber optic cameras in close environments such as plastic pipes, and, more generally, to create a magnetic guidance path by creating a traction force between a leader magnet and a following magnet. In each case, the sensor of the present invention provides an indication when the leader magnet is in the traction position.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. Apparatus for intubating a patient to introduce nutrition into the small intestine, comprising:

an elongated flexible catheter having a ferrous metal follower at a distal end portion thereof, said catheter having an access channel extending to a lumen for conducting a nutrient to an eyelet communicating with said lumen at said distal end of said catheter upstream of said ferrous metal follower;

a leader magnet having a magnetic field of a predetermined magnetic flux associated therewith, the magnetic flux of said leader magnet permeating body tissue of the abdomen and said ferrous metal follower and thereby establishing a magnetic coupling between said ferrous metal follower and said leader magnet at a predetermined distance between said ferrous metal follower and said leader magnet, the magnetic coupling causing said ferrous metal follower to move in response to movement of said leader magnet; and a shielded magnetic reed switch positioned adjacent said ferrous metal follower, wherein said shielded magnetic reed switch actuates within the predetermined distance to indicate establishment of the magnetic coupling.

2. The apparatus of claim 1, wherein said shielded magnetic reed switch comprises a magnetic reed switch having a pair of overlapping reeds sealed in a glass envelope, said overlapping reeds being characterized as having external portions for connection to an electrical circuit, wherein said magnetic reed switch is disposed within a ferrous metal housing and said ferrous metal housing shields said magnetic reed switch from magnetic flux.

3. The apparatus of claim 2, wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to an electrical circuit.

4. The apparatus of claim 3, wherein said ferrous metal housing includes a thickened end portion adjacent said closed end of said ferrous metal housing.

5. The apparatus of claim 4, wherein said tubular wall is about 0.0125 inches thick and said thickened end portion is about 0.125 inches thick.

6. The apparatus of claim 4, wherein said tubular wall is about 0.025 inches thick and said thickened end portion is about 0.125 inches thick.

7. The apparatus of claim 4, wherein said tubular wall is about 0.025 inches thick, said tubular wall has an outer diameter of about 0.151 inches, and said thickened end portion is about 0.125 inches thick.

8. The apparatus of claim 3, further comprising heat shrink applied to said solder connections.

9. The apparatus of claim 8, further comprising potting compound surrounding said magnetic reed switch and said solder connections within said ferrous metal housing, said potting compound thereby holding said reed switch and said electrical leads securely within said ferrous metal housing.

10. The apparatus of claim 2, wherein said magnetic reed switch is a single-pole, single-throw, normally-open reed switch.

11. The apparatus of claim 2, wherein said magnetic reed switch is a single-pole, single-throw, normally-closed reed switch.

12. The apparatus of claim 2, wherein said magnetic reed switch is a single-pole, double-throw, break-before-make reed switch.

13. The apparatus of claim 1, wherein said shielded magnetic reed switch further comprises:

a magnetic reed switch which actuates at distances greater than the predetermined distance between said ferrous metal follower and said leader magnet; and a ferrous metal housing, said magnetic reed switch being disposed within said ferrous metal housing, whereby said ferrous metal housing shields said magnetic reed switch from said leader magnet and prevents said magnetic reed switch from actuating at distances greater than the predetermined distance between said ferrous metal follower and said leader magnet.

14. The apparatus of claim 13, wherein said magnetic reed switch further comprises a pair of overlapping reeds sealed in a glass envelope, said overlapping reeds being characterized as having external portions, and wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to an electrical circuit.

15. The apparatus of claim 14, wherein said ferrous metal housing includes a thickened end portion adjacent said closed end of said ferrous metal housing.

16. The apparatus of claim 15, wherein said tubular wall is about 0.0125 inches thick and said thickened end portion is about 0.125 inches thick.

17. The apparatus of claim 15, wherein said tubular wall is about 0.025 inches thick and said thickened end portion is about 0.125 inches thick.

18. The apparatus of claim 15, wherein said tubular wall is about 0.025 inches thick, said tubular wall has an outer diameter of about 0.151 inches, and said thickened end portion is about 0.125 inches thick.

19. The apparatus of claim 14, further comprising heat shrink surrounding said solder connections.

20. The apparatus of claim 19, further comprising potting compound applied to said magnetic reed switch and said solder connections within said ferrous metal housing, said potting compound thereby holding said reed switch and said electrical leads securely within said ferrous metal housing.

21. The apparatus of claim 13, wherein said magnetic reed switch is a single-pole, single-throw, normally-open reed switch.

22. The apparatus of claim 13, wherein said magnetic reed switch is a single-pole, single-throw, normally-closed reed switch.

23. The apparatus of claim 13, wherein said magnetic reed switch is a single-pole, double-throw, break-before-make reed switch.

24. The apparatus of claim 2, wherein said ferrous metal housing also provides said ferrous metal follower.

25. Apparatus for intubating a patient to introduce nutrition into the small intestine, comprising:

an elongated flexible catheter having a ferrous metal follower at a distal end portion thereof, said catheter having an access channel extending to a lumen for conducting a nutrient to an eyelet communicating with said lumen at said distal end of said catheter upstream of said ferrous metal follower;

a leader magnet having a magnetic field of a predetermined magnetic flux associated therewith, the magnetic flux of said leader magnet permeating body tissue of the abdomen and said ferrous metal follower and thereby establishing a magnetic coupling between said ferrous metal follower and said leader magnet at a predetermined distance between said ferrous metal follower and said leader magnet, the magnetic coupling causing said ferrous metal follower to move in response to movement of said leader magnet; and a sensor positioned adjacent said ferrous metal follower for detecting the presence of said leader magnet at the predetermined distance between said ferrous metal follower and said leader magnet, and wherein said sensor is connected to an electrical circuit, said sensor comprising:

a ferrous metal housing;

a magnetic reed switch having a predetermined magnetic flux requirement for actuation of said magnetic reed switch, said magnetic reed switch being disposed within said ferrous metal housing, wherein said ferrous metal housing shields said magnetic reed switch from the magnetic flux associated with said leader magnet until said ferrous metal housing is fully saturated and the predetermined magnetic flux requirement is available within said ferrous metal housing to actuate said magnetic reed switch, thereby providing an input to the electrical circuit.

26. The apparatus of claim 25, wherein said magnetic reed switch further comprises a pair of overlapping reeds sealed in a glass envelope, said overlapping reeds being characterized as having external portions, wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to the electrical circuit.

27. The apparatus of claim 26, wherein said ferrous metal housing includes a thickened end portion adjacent said closed end of said ferrous metal housing.

28. The apparatus of claim 27, wherein said tubular wall is about 0.0125 inches thick and said thickened end portion is about 0.125 inches thick.

29. The apparatus of claim 27 wherein said tubular wall is about 0.025 inches thick and said thickened end portion is about 0.125 inches thick.

30. The apparatus of claim 27, wherein said tubular wall is about 0.025 inches thick, said tubular wall has an outer diameter of about 0.151 inches, and said thickened end portion is about 0.125 inches thick.

31. The apparatus of claim 26, further comprising heat shrink applied to said solder connections.

32. The apparatus of claim 31, further comprising potting compound surrounding said magnetic reed switch and said solder connections within said ferrous metal housing, said potting compound thereby holding said reed switch and said electrical leads securely within said ferrous metal.

33. The apparatus of claim 25, wherein said magnetic reed switch is a single-pole, single-throw, normally-open reed switch.

34. The apparatus of claim 25, wherein said magnetic reed switch is a single-pole, single-throw, normally-closed reed switch.

35. The apparatus of claim 25, wherein said magnetic reed switch is a single-pole, double-throw, break-before-make reed switch.

36. The apparatus of claim 25, wherein said ferrous metal housing further provides said ferrous metal follower.

37. Apparatus for intubating a patient to introduce nutrition into the small intestine, comprising:

an elongated flexible catheter having a follower magnet at a distal end portion thereof, said catheter having an access channel extending to a lumen for conducting a nutrient to an eyelet communicating with said lumen at said distal end of said catheter upstream of said follower magnet;

a leader magnet having a magnetic field of a predetermined magnetic flux associated therewith, the magnetic flux of said leader magnet permeating body tissue of the abdomen and said follower magnet and thereby establishing a magnetic coupling between said follower magnet and said leader magnet at a predetermined distance between said follower magnet and said leader magnet, the magnetic coupling causing said follower magnet to move in response to movement of said leader magnet; and a shielded magnetic reed switch positioned adjacent said follower magnet, wherein said shielded magnetic reed switch actuates within the predetermined distance between said follower magnet and said leader magnet to indicate establishment of the magnetic coupling.

38. The apparatus of claim 37, wherein said shielded magnetic reed switch comprises a magnetic reed switch having a pair of overlapping reeds sealed in a glass envelope, said overlapping reeds being characterized as having external portions for connection to an electrical circuit, wherein said magnetic reed switch is disposed within a ferrous metal housing and said ferrous metal housing shields said magnetic reed switch from magnetic flux.

39. The apparatus of claim 38, wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to an electrical circuit.

40. The apparatus of claim 39, wherein said ferrous metal housing includes a thickened end portion adjacent said closed end of said ferrous metal housing.

41. The apparatus of claim 40, wherein said tubular wall is about 0.0125 inches thick and said thickened end portion is about 0.125 inches thick.

42. The apparatus of claim 40, wherein said tubular wall is about 0.025 inches thick and said thickened end portion is about 0.125 inches thick.

43. The apparatus of claim 40, wherein said tubular wall is about 0.025 inches thick, said tubular wall has an outer diameter of about 0.151 inches, and said thickened end portion is about 0.125 inches thick.

44. The apparatus of claim 39, further comprising heat shrink applied to said solder connections.

45. The apparatus of claim 44, further comprising potting compound surrounding said magnetic reed switch and said solder connections within said ferrous metal housing, said potting compound thereby holding said reed switch and said electrical leads securely within said ferrous metal housing.

46. The apparatus of claim 38, wherein said magnetic reed switch is a single-pole, single-throw, normally-open reed switch.

47. The apparatus of claim 38, wherein said magnetic reed switch is a single-pole, single-throw, normally-closed reed switch.

48. The apparatus of claim 38, wherein said magnetic reed switch is a single-pole, double-throw, break-before-make reed switch.

49. The apparatus of claim 37, wherein said shielded magnetic reed switch further comprises:
   a magnetic reed switch which actuates at distances greater than the predetermined distance between said follower magnet and said leader magnet; and
   a ferrous metal housing, said magnetic reed switch being disposed within said ferrous metal housing, whereby said ferrous metal housing shields said magnetic reed switch from said leader magnet and prevents said magnetic reed switch from actuating at distances greater than the predetermined distance between said follower magnet and said leader magnet.

50. The apparatus of claim 49, wherein said magnetic reed switch further comprises a pair of overlapping reeds sealed in a glass envelope, said overlapping reeds being characterized as having external portions, and wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to an electrical circuit.

51. The apparatus of claim 50, wherein said ferrous metal housing includes a thickened end portion adjacent said closed end of said ferrous metal housing.

52. The apparatus of claim 51, wherein said tubular wall is about 0.0125 inches thick and said thickened end portion is about 0.125 inches thick.

53. The apparatus of claim 51 wherein said tubular wall is about 0.025 inches thick and said thickened end portion is about 0.125 inches thick.

54. The apparatus of claim 51, wherein said tubular wall is about 0.025 inches thick, said tubular wall has an outer diameter of about 0.151 inches, and said thickened end portion is about 0.125 inches thick.

55. The apparatus of claim 50, further comprising heat shrink surrounding said solder connections.

56. The apparatus of claim 55, further comprising potting compound applied to said magnetic reed switch and said solder connections within said ferrous metal housing, said potting compound thereby holding said reed switch and said electrical leads securely within said ferrous metal housing.

57. The apparatus of claim 49, wherein said magnetic reed switch is a single-pole, single-throw, normally-open reed switch.

58. The apparatus of claim 49, wherein said magnetic reed switch is a single-pole, single-throw, normally-closed reed switch.

59. The apparatus of claim 49, wherein said magnetic reed switch is a single-pole, double-throw, break-before-make reed switch.

60. Apparatus for intubating a patient to introduce nutrition into the small intestine, comprising:
   an elongated flexible catheter having a follower magnet at a distal end portion thereof, said catheter having an access channel extending to a lumen for conducting a nutrient to an eyelet communicating with said lumen at said distal end of said catheter upstream of said follower magnet;
   a leader magnet having a magnetic field of a predetermined magnetic flux associated therewith, the magnetic flux of said leader magnet permeating body tissue of the abdomen and said follower magnet and thereby establishing a magnetic coupling between said follower magnet and said leader magnet at a predetermined distance between said follower magnet and said leader magnet, the magnetic coupling causing said follower magnet to move in response to movement of said leader magnet; and
   a sensor positioned adjacent said follower magnet for detecting the presence of said leader magnet at the predetermined distance between said follower magnet and said leader magnet, and wherein said sensor is connected to an electrical circuit, said sensor comprising:
      a ferrous metal housing;
      a magnetic reed switch having a predetermined magnetic flux requirement for actuation of said magnetic reed switch, said magnetic reed switch being disposed within said ferrous metal housing, wherein said ferrous metal housing shields said magnetic reed switch from the magnetic flux associated with said leader magnet until said ferrous metal housing is fully saturated and the predetermined magnetic flux requirement is available within said ferrous metal housing to actuate said magnetic reed switch, thereby providing an input to the electrical circuit.

61. The apparatus of claim 60, wherein said magnetic reed switch further comprises a pair of overlapping reeds sealed in a glass envelope, said overlapping reeds being characterized as having external portions, wherein said ferrous metal housing consists of a tubular wall connecting an open end and a closed end, wherein electrical leads are soldered to said external portions of said reeds to form solder connections and, further, wherein said electrical leads extend from said open end of said ferrous metal housing for connection to the electrical circuit.

62. The apparatus of claim 61, wherein said ferrous metal housing includes a thickened end portion adjacent said closed end of said ferrous metal housing.

63. The apparatus of claim 62, wherein said tubular wall is about 0.0125 inches thick and said thickened end portion is about 0.125 inches thick.

64. The apparatus of claim 62 wherein said tubular wall is about 0.025 inches thick and said thickened end portion is about 0.125 inches thick.

65. The apparatus of claim 62, wherein said tubular wall is about 0.025 inches thick, said tubular wall has an outer diameter of about 0.151 inches, and said thickened end portion is about 0.125 inches thick.

66. The apparatus of claim 61, further comprising heat shrink applied to said solder connections.

67. The apparatus of claim 62, further comprising potting compound surrounding said magnetic reed switch and said solder connections within said ferrous metal housing, said potting compound thereby holding said reed switch and said electrical leads securely within said ferrous metal.

68. The apparatus of claim 60, wherein said magnetic reed switch is a single-pole, single-throw, normally-open reed switch.

69. The apparatus of claim 60, wherein said magnetic reed switch is a single-pole, single-throw, normally-closed reed switch.

70. The apparatus of claim 60, wherein said magnetic reed switch is a single-pole, double-throw, break-before-make reed switch.

* * * * *

UNITED STATES PATENT AND TRADEMARK OFFICE
Certificate

Patent No. 6,126,647                                                                   Patented: October 3, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Tyler Posey, Blanchard, OK; Raymond Lee Morgan, Norman, OK; and Sabry A. Gabriel, Lizelle, GA.

Signed and Sealed this Twenty-third Day of August 2005.

<div style="text-align:right">

BRIAN L. CASLER
*Supervisory Patent Examiner*
Art Unit 3763

</div>